United States Patent [19]

West et al.

[11] Patent Number: 5,077,525
[45] Date of Patent: Dec. 31, 1991

[54] ELECTRODELESS CONDUCTIVITY SENSOR WITH INFLATABLE SURFACE

[75] Inventors: Barry R. West, Santa Ana; Wayne B. Wood, Silverado; Mark C. Okel, Mission Viejo, all of Calif.

[73] Assignee: Rosemount Inc., Eden Prairie, Minn.

[21] Appl. No.: 469,200

[22] Filed: Jan. 24, 1990

[51] Int. Cl.⁵ ............................................. G01N 27/02
[52] U.S. Cl. .................................... 324/445; 324/204
[58] Field of Search ............... 324/445, 446, 447, 225, 324/226, 262, 204, 450; 73/866.5

[56] References Cited

U.S. PATENT DOCUMENTS

| | | | |
|---|---|---|---|
| 2,271,760 | 2/1942 | Colley | 244/134 |
| 2,375,146 | 5/1945 | Taylor | 244/134 |
| 2,542,057 | 2/1951 | Relis | 324/445 |
| 2,560,287 | 7/1951 | Harper | 244/134 |
| 2,567,804 | 9/1951 | Davies | 244/134 |
| 3,603,873 | 9/1971 | Cirulis | 324/30 |
| 3,930,493 | 1/1976 | Williamson | 128/2.05 |
| 4,100,491 | 7/1978 | Newman, Jr. et al. | 324/204 |
| 4,220,920 | 9/1980 | Gross | 324/442 |
| 4,508,295 | 4/1985 | Cattaneo et al. | 244/134 |
| 4,595,442 | 6/1986 | Trares et al. | 156/286 |
| 4,706,911 | 11/1987 | Briscoe et al. | 244/134 |
| 4,779,823 | 10/1988 | Ely et al. | 244/134 |
| 4,836,474 | 6/1989 | Briscoe et al. | 244/134 |

FOREIGN PATENT DOCUMENTS 776861  6/1957  United Kingdom ................ 324/445

OTHER PUBLICATIONS

*Scientific Encyclopedia*, Sixth Edition, Considine (Van Nostrand 1983).
*Electrochemical Methods of Process Analysis*, D. E. Smith et al. (Instrument Society of America 1972).

Primary Examiner—Kenneth A. Wieder
Assistant Examiner—Maura K. Regan
Attorney, Agent, or Firm—Kinney & Lange

[57] ABSTRACT

An inductive conductivity sensor is immersed in a liquid to measure its conductivity. The sensor comprises a transducer for generating a changing magnetic field and for inductively measuring an electric current induced in the liquid by the changing magnetic field. The transducer has an external surface facing the liquid. A elastic membrane separates the external surface from the liquid. The elastic membrane is periodically inflated and deflated to deform its outer shape and thereby remove deposits formed on the membrane.

33 Claims, 3 Drawing Sheets

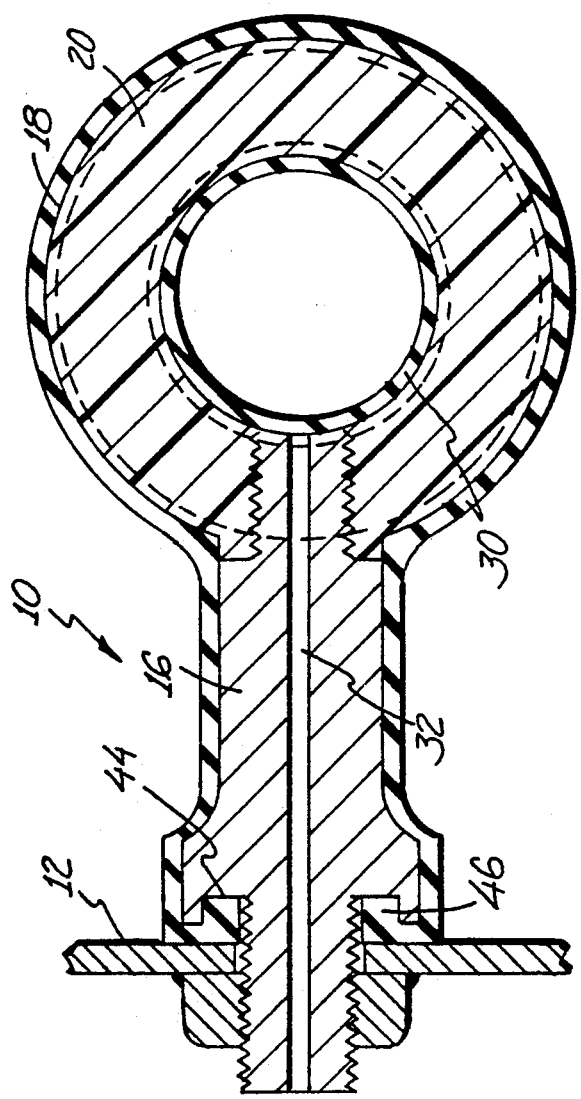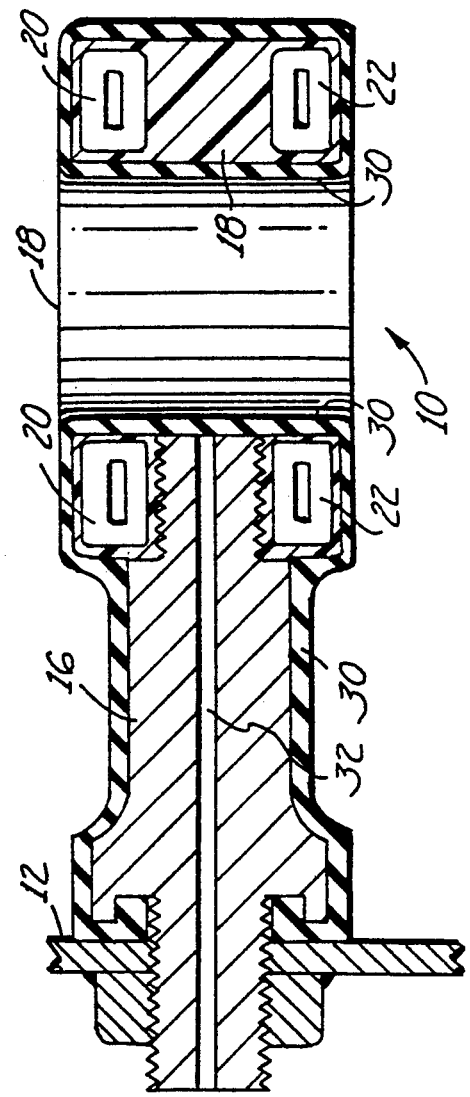

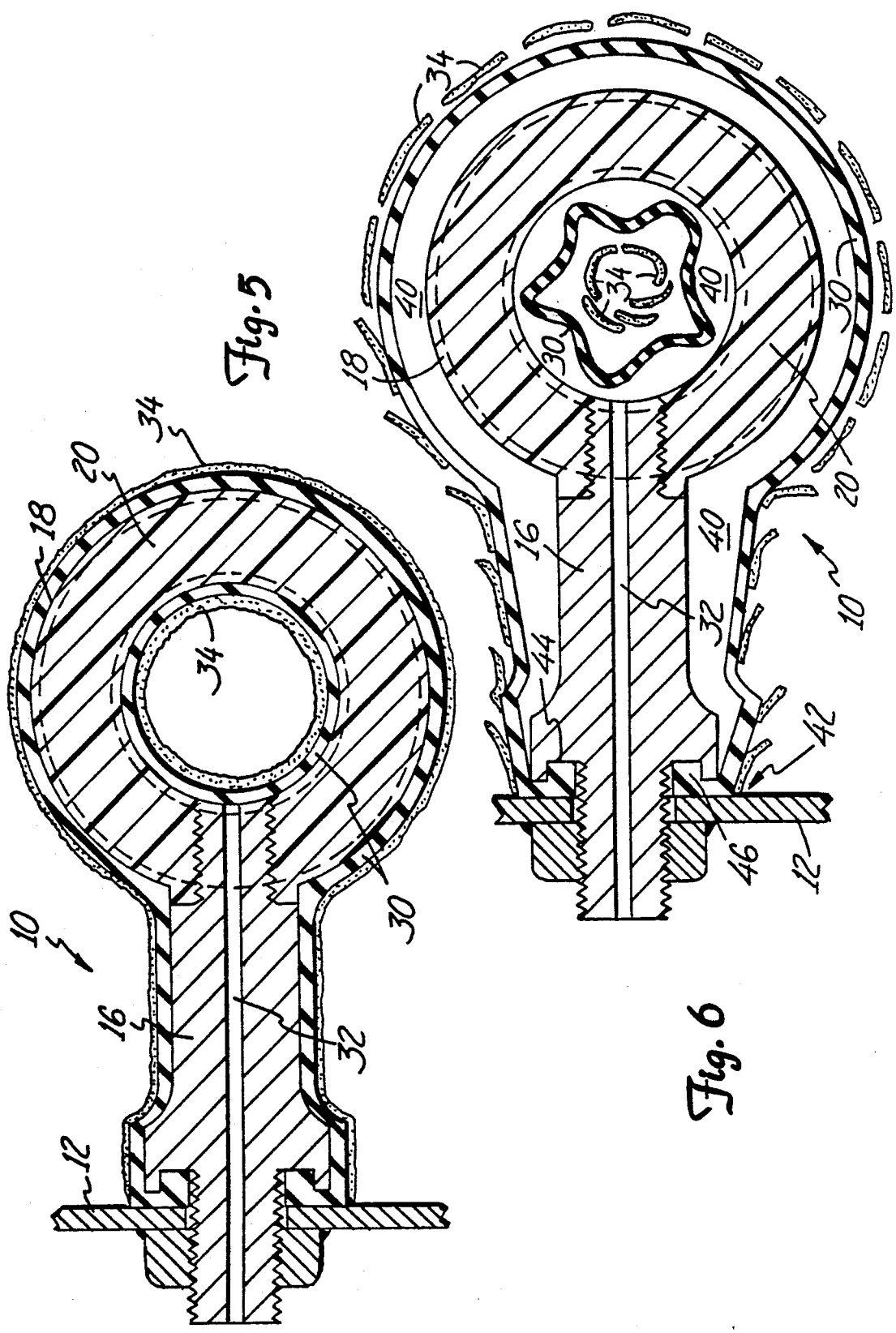

ELECTRODELESS CONDUCTIVITY SENSOR WITH INFLATABLE SURFACE

The present invention relates to electrodeless conductivity sensors used for determining fluid conductivity. In particular, this invention relates to a self-cleaning sensor having an elastic exterior membrane.

Electrodeless conductivity measuring sensors are well known in the art and are used to measure the conductivity of a fluid, such as a liquid or a dispersion of solids suspended in a liquid. Conductivity sensors are used as a means of investigating the properties of electrolytes in solution, such as the degree of disassociation, the formation of chemical complexes, and hydrolysis.

An electrodeless conductivity sensor includes two "toroidal" transformer coils which are immersed in the liquid to be measured. The first coil is electrically excited by an alternating current source to generate a changing magnetic field. The changing magnetic field induces an electrical current loop in the liquid. In electrolytic solutions, the mechanism of electrical current transfer is dependent on ions. The magnitude of the induced current is indicative of the conductivity of the liquid. The second coil detects the magnitude of the induced current. Electrodeless conductivity sensors are often called toroidal conductivity sensors because of the general shape of the transformer coils.

The conductivity of a fluid may also be used to measure a wide variety of other parameters, such as the amount of contaminants in drinking water and a measure of chemical concentrations in industrial process streams. Applications such as these involve the determination of conductivities in many different physical environments.

In some environments, toroidal conductivity sensors are subject to coating or clogging from deposits or solid materials. Deposits can accumulate on the exterior of the sensor and, if electrically conductive, the deposits form a conductive path electrically in parallel with the current loop in the liquid. If the deposits are electrically non-conductive, they can reduce the cross sectional area or increase the length of the electrical current loop in the liquid. Either conductive or non-conductive deposits can thus adversely affect measurement accuracy by increasing or decreasing current flow around the surfaces of the sensor.

As a result, prior art conductivity sensors must be periodically removed and cleaned to maintain measurement accuracy. The extra steps required to remove the sensor for cleaning are a disadvantage and may be very costly, depending upon the particular application in which the sensor is used. In fact, entire manufacturing processes may be required to shut down simply to clean a single sensor.

In one attempt at eliminating these costs, a coat of antifouling paint is applied on the sensor surface. The antifouling paint allows the sensor to be immersed continually in sea water without accumulation of marine growth. This method is not effective, however, in applications where a variety of deposits can accumulate on the sensor surface. The prior art lacks a self-cleaning toroidal conductivity sensor effective in a variety of applications.

SUMMARY OF THE INVENTION

The inductive conductivity sensor of the present invention is immersed in a liquid to measure its conductivity. The sensor comprises a transducer for generating a changing magnetic field and for inductively measuring an electric current induced in the liquid by the changing magnetic field. The transducer includes an external surface facing the liquid. In the present invention, an elastic membrane separates the external surface of the transducer from the liquid. The elastic membrane is periodically inflated to remove deposits formed on the membrane.

In a preferred embodiment, the sensor includes a passage through the transducer to an opening at an interface between the transducer and the elastic membrane. The passage provides a channel for routing pressurized fluid to the interface for inflating the membrane. The fluid may include either a liquid or a gas.

BRIEF DESCRIPTION OF THE DRAWINGS

FIG. 3 is a cross-sectional view of the sensor as seen from line 3—3 of FIG. 1.

FIG. 4 is a cross-sectional view of the sensor taken along line 4—4 of FIG. 2.

FIG. 5 is a view similar to FIG. 3, but having deposits formed on an elastic membrane.

FIG. 6 is a view similar to FIG. 5, but having the elastic membrane in an inflated state.

DETAILED DESCRIPTION OF THE PREFERRED EMBODIMENTS

Figure 1:
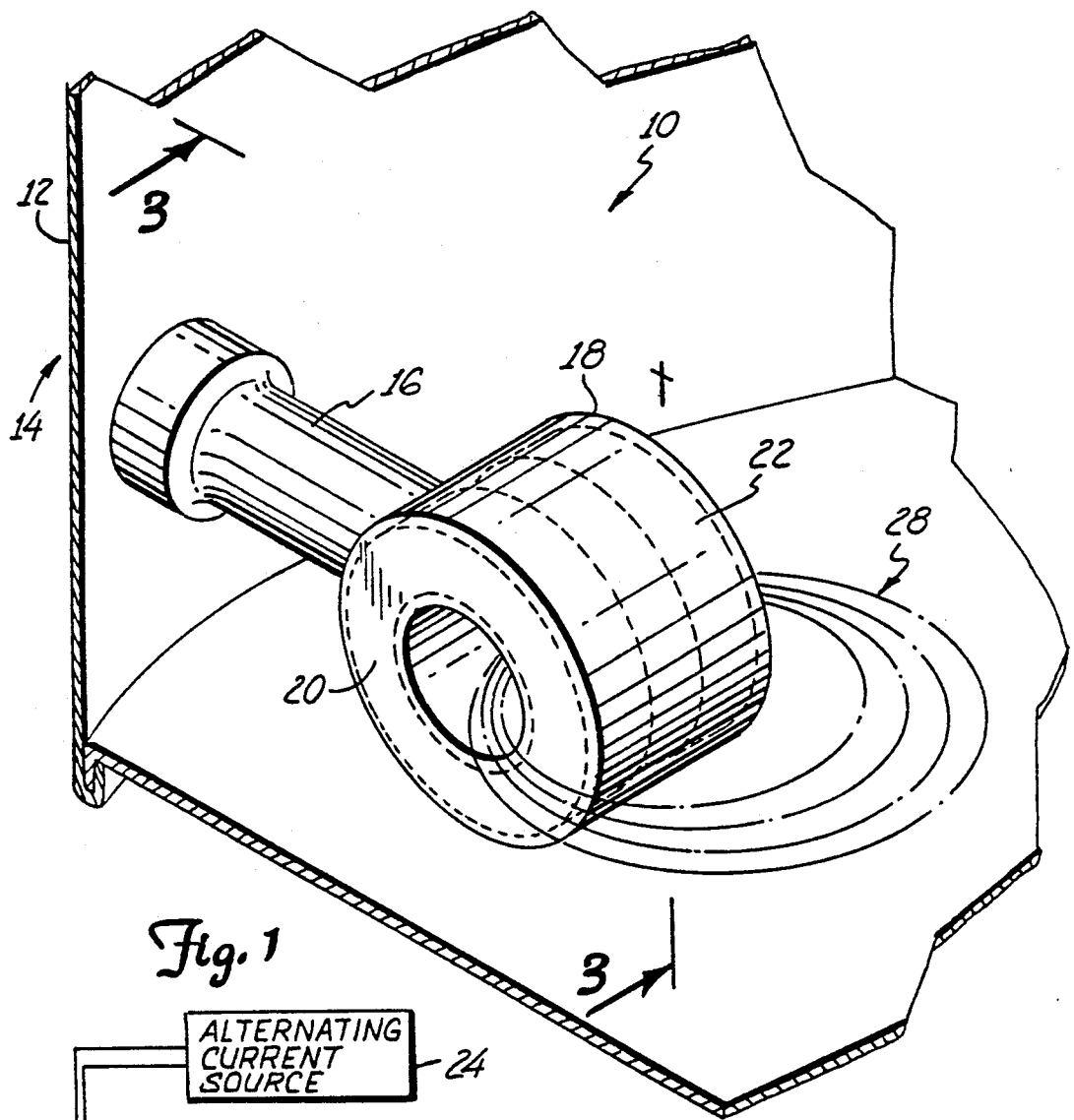
FIG. 1 is a perspective view of an inductive conductivity sensor mounted to a wall of a container.

FIG. 1 is a perspective view of an inductive conductivity sensor. Sensor 10 is mounted to wall 12 of container 14. Sensor 10 includes arm or strut 16 and body 18. Strut 16 has a proximal end and a distal end. The proximal end is threaded and secured to wall 12. The distal end supports body 18 within container 14. Alternatively, sensor 10 may be mounted to a wall within a pipe, a tank, or a chemical process stream, for example.

Body 18 supports first and second toroidal coils 20 and 22 (shown in phantom). First and second toroidal coils 20 and 22 each have electrical wires (not shown) wrapped around toroidal ferromagnetic cores. First toroidal coil 20 is electrically coupled to alternating current source 24 (shown in FIG. 2). Second toroidal coil 22 is electrically coupled to measurement circuit 26 (also shown in FIG. 2).

Figure 2:
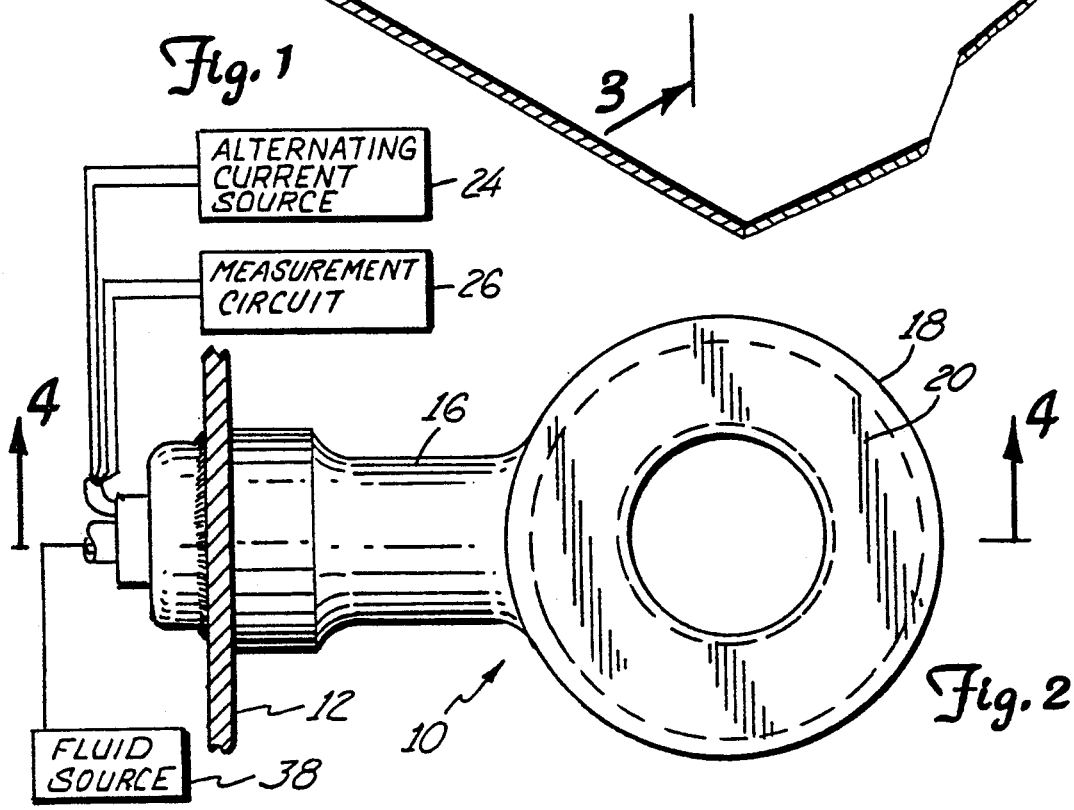
FIG. 2 is a view in side elevation of the sensor of FIG. 1.

During operation, sensor 10 is immersed in an electrolytic liquid within container 14. Alternating current source 24 electrically excites first toroidal coil 20 to generate a changing magnetic field which induces electrical current loop 28 in the liquid. The magnitude of current loop 28 is representative of the conductivity of the liquid. Current loop 28 subsequently induces a current in second toroidal coil 22. The induced current in coil 22 is indicative of the conductivity of the liquid and is measured by measurement circuit 26. Sensors of the type shown in FIG. 1 and 2 are referred to in the art as toroidal conductivity sensors because of the general shape of the transformer coils.

FIG. 3 and 4 are sectional views of sensor 10. FIG. 3 is taken along line 3—3 of FIG. 1. FIG. 4 is taken along line 4—4 of FIG. 2. Sensor 10 includes strut 16, body 18, first and second toroidal coils 20 and 22, elastic membrane 30, and passage 32. The external surfaces of strut 16 and body 18 are provided with a smooth, rounded shape suitable for receiving the elastic membrane by molding them with a relatively hard plastic. As an alternative to molding, strut 16 and body 18 can be formed with a metal housing, provided that it is split into two portions so that it does not form a shorted turn around first toroidal coil 20 and second toroidal coil 22. Strut 16 and body 18 can also be assembled from machined, molded, or cast parts.

Elastic membrane 30 is formed on the surface of sensor 10. When sensor 10 is immersed in the liquid within container 14 (shown in FIG. 1), membrane 30 separates the sensor from the liquid. Strut 16 includes groove 44 that accepts ring 46 of membrane 30. Ring 46 creates an airtight seal when strut 16 is secured to wall 12. In some applications, deposits or solid material may form on the surface of membrane 30 after immersion for an extended period of time.

FIG. 5 is a view similar to FIG. 3, but illustrating deposits 34 formed on the surface of membrane 30. Deposits 34 can interfere with electrical current loop 28 (shown in FIG. 1) which measures conductivity of the liquid. Prior art sensors must be removed from the liquid and then cleaned to remove the deposits.

With the present invention, in contrast, sensor 10 may be cleaned without removal. Passage 32 provides a channel in which pressurized fluid can be forced through strut 16 to an opening at an interface between body 18 and elastic membrane 30. The fluid may be a liquid or a gas. The fluid is supplied by a controlled fluid source such as fluid source 38 shown in FIG. 2. Typically, the fluid is compressed air and fluid source 38 is a plant compressed air line.

FIG. 6 illustrates membrane 30 inflated by pressurized fluid 40. The pressure of fluid 40 must exceed the process pressure to inflate membrane 30. Preferably, the pressure of fluid 40 exceeds the process pressure by about 5 psi to about 20 psi. Alternatively, if the fluid is a liquid, a fixed volume of liquid can be pumped into and out of passage 32 to inflate and deflate membrane 30. During inflation, brittle or crusty deposits 34 will tend to break off the membrane surface. Even soft clogging materials, such as pulp stock, will tend to be squeezed and displaced from the surface. To facilitate inflation, membrane 30 is sealed at interface 42 between wall 12 and strut 16.

At the end of a cleaning cycle, pressurized fluid 40 (e.g. air) is removed from passage 32 and membrane 30 returns to its original shape shown in FIGS. 3–5. The cleaning cycle may be repeated periodically to maintain sensor accuracy. In one embodiment, controlled fluid source 38 initiates periodic cleaning cycles.

Membrane 30 is molded from a suitable material which is resilient, electrically insulating, non-porous and forms a smooth surface when molded. The material is selected to be compatible with the process conditions for each selected application, i.e., process fluid characteristics, pH, temperature range, available air pressure for inflation, and so forth. Suitable materials can include vulcanized rubber, and various synthetic elastomers, including polyurethanes, Thiokol rubbers, polyacrylate elastomers, silicone elastomers, fluorelastomers, ethylene-polypropylene elastomers, and styrene-butadiene (SBR) rubbers depending on the application. A preferred material for the membrane is ethylene polypropylene rubber. The thickness of the membrane can be adjusted according to the application, and is preferably in the range of about 2 mm to 3 mm.

The present invention provides a self-cleaning inductive conductivity sensor which does not have to be removed from a process, or application, to be cleaned. The present invention significantly reduces maintenance costs associated with conductivity sensors of the prior art.

In the embodiment shown, the membrane is inflated to provide cleaning, and deflated during normal operation. It is also within the scope of the invention to provide an inflated membrane during normal operation, and a deflated membrane to provide cleaning.

Although the present invention has been described with reference to preferred embodiments, workers skilled in the art will recognize that changes may be made in form and detail without departing from the spirit and scope of the invention.

What is claimed is:

1. An inductive conductivity sensor for communicating with a liquid to measure its conductivity, the sensor comprising:

a transducer for generating a changing magnetic field and for inductively measuring an electric current induced in the liquid by the changing magnetic field, the transducer having an external surface facing the liquid;

an elastic membrane separating the external surface from the liquid; and means for inflating and deflating the elastic membrane such that the membrane is changed in shape to remove deposits formed on the membrane.

2. The inductive conductivity sensor of claim 1 wherein the elastic membrane comprises a vulcanized rubber boot formed over the transducer.

3. The inductive conductivity sensor of claim 1 wherein the elastic membrane comprises a synthetic elastomer sleeve formed over the transducer.

4. The inductive conductivity sensor of claim 1 wherein the elastic membrane has a thickness of about 2 mm to about 3 mm.

5. The inductive conductivity sensor of claim 1 wherein the means for inflating and deflating includes a passage through the transducer to an opening in an interface between the transducer and the elastic membrane, the passage for routing pressurized fluid to the interface for inflating and deflating the elastic membrane.

6. The inductive conductivity sensor of claim 5 and further comprising a controlled fluid source for forcing pressurized fluid through the passage to inflate and deflate the elastic membrane.

7. The inductive conductivity sensor of claim 6 wherein the pressurized fluid is pressurized in excess of a process pressure by about 5 psi to about 20 psi.

8. The inductive conductivity sensor of claim 6 wherein the controlled fluid source pumps a specified amount of fluid into and out of the passage to inflate and deflate the membrane.

9. The inductive conductivity sensor of claim 6 wherein the pressurized fluid comprises a liquid.

10. The inductive conductivity sensor of claim 6 wherein the pressurized fluid comprises a gas.

11. The inductive conductivity sensor of claim 1 wherein the transducer comprises a plurality of toroidal transformer coils, each having at least one electrical conductive winding being wound around a toroidal core of ferromagnetic material.

12. A self-cleaning inductive conductivity transducer for immersion in a liquid to measure conductivity of the liquid, the transducer comprising:

electromagnetic means for generating a changing magnetic field and for inductively measuring an electric current induced in the liquid by the changing magnetic field; and means for deforming an exterior shape of the transducer to remove deposits formed on the transducer.

13. The self-cleaning inductive conductivity transducer of claim 12 wherein the transducer further comprises an external surface facing the liquid, and the means for deforming comprises:

an elastic membrane separating the external surface from the liquid; and means for inflating and deflating the elastic membrane such that the shape of the membrane is changed to remove deposits formed on the membrane.

14. The self-cleaning inductive conductivity transducer of claim 13 wherein the elastic membrane further comprises a synthetic elastomer formed over the transducer.

15. The self-cleaning inductive conductivity transducer of claim 13 wherein the elastic membrane has a thickness of about 2 mm to about 3 mm.

16. The self-cleaning inductive conductivity transducer of claim 13 wherein the means for inflating and deflating further includes a passage through the transducer to an opening in an interface between the transducer and the elastic membrane, the passage adapted for routing pressurized fluid to the interface to inflate and deflate the elastic membrane.

17. The self-cleaning inductive conductivity sensor of claim 16 wherein the pressurized fluid is pressurized in excess of a process pressure by about 5 psi to about 20 psi.

18. The self-cleaning inductive conductivity sensor of claim 16 wherein the means for inflating and deflating further comprises a controlled fluid source for forcing pressurized fluid through the passage to inflate and deflate the elastic membrane.

19. The self-cleaning inductive conductivity sensor of claim 18 wherein the controlled fluid source pumps a specified amount of fluid into and out of the passage to inflate and deflate the elastic membrane.

20. The self-cleaning inductive conductivity transducer of claim 16 wherein the pressurized fluid comprises a liquid.

21. The self-cleaning inductive conductivity transducer of claim 16 wherein the pressurized fluid comprises a gas.

22. The self-cleaning inductive conductivity transducer of claim 12 wherein the electromagnetic means further comprises a plurality of toroidal transformer coils, each having at least one electrical conductive winding wound around a toroidal core of ferromagnetic material.

23. An inductive conductivity sensor for communicating with a liquid to measure its conductivity, the sensor comprising:

a first toroidal transformer coil for generating a changing magnetic field which induces an electric current in the liquid, the electric current having a magnitude indicative of the conductivity;

a second toroidal transformer coil for sensing the electric current and for generating an output current representative of the conductivity;

a body supporting the first and second transformer coils, the body having an external surface facing the liquid;

an elastic membrane separating the external surface from the liquid; and a passage through the body to an interface between the body and the elastic membrane for permitting pressurized fluid to inflate and deflate the elastic membrane around the body and to thereby dislodge deposits formed on the elastic membrane.

24. The inductive conductivity sensor of claim 23 wherein the elastic membrane comprises a vulcanized rubber boot formed over the body.

25. The inductive conductivity sensor of claim 23 wherein the elastic membrane comprises a synthetic elastomer.

26. The inductive conductivity sensor of claim 23 wherein the pressurized gas comprises a liquid.

27. The inductive conductivity sensor of claim 23 wherein the pressurized fluid comprises a gas.

28. A method of cleaning an inductive conductivity transducer immersed in a liquid without removing the transducer from the liquid, the method comprising:

deforming an exterior shape of the transducer to remove deposits formed on the transducer.

29. The method of claim 28 and further comprising the step of providing an elastic membrane over an external surface of the transducer, prior to immersion, for separating the transducer from the liquid.

30. The method of claim 29 wherein deforming the shape of the transducer further comprises the step of inflating and deflating the elastic membrane to change its shape and to thereby dislodge deposits formed on the membrane.

31. The method of claim 30 wherein the step of inflating and deflating comprises pumping a specified amount of fluid into and out of an interface between the transducer and the elastic membrane to inflate and deflate the membrane around the transducer.

32. The method of claim 30 wherein the step of inflating and deflating comprises routing fluid having a pressure greater than a process pressure to an interface between the transducer and the elastic membrane.

33. An inductive conductivity sensor for communicating with a liquid to measure its conductivity, the sensor comprising:

a first toroidal transformer coil for generating a changing magnetic field which induces an electric current in the liquid, the electric current having a magnitude indicative of the conductivity;

a second toroidal transformer coil for sensing the electric current and for generating an output current representative of the conductivity;

a strut having a proximate end and a distal end, the proximate end being threaded to allow attachment of the strut within a container holding the liquid;

a body supported at the distal end of the strut and carrying the first and second transformer coils;

an elastic membrane separating the strut and the body from the liquid;

a passage through the strut and the body to an interface between the body and the elastic membrane; and a controlled fluid source for forcing pressurized fluid through the passage to inflate and deflate the elastic membrane to thereby dislodge deposits formed on the elastic membrane.

* * * * *